US012608768B2

(12) United States Patent
Kim et al.

(10) Patent No.: US 12,608,768 B2
(45) Date of Patent: Apr. 21, 2026

(54) HYPERSPECTRAL LEARNING FOR INSTANTANEOUS SPATIOSPECTRAL IMAGING OF HEMODYNAMICS

(71) Applicant: Purdue Research Foundation, West Lafayette, IN (US)

(72) Inventors: Young L Kim, West Lafayette, IN (US); Yuhyun Ji, West Lafayette, IN (US); Sang Mok Park, West Lafayette, IN (US); Semin Kweon, West Lafayette, IN (US); Jungwoo Leem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 292 days.

(21) Appl. No.: 18/423,669

(22) Filed: Jan. 26, 2024

(65) Prior Publication Data

US 2024/0273677 A1 Aug. 15, 2024

Related U.S. Application Data

(60) Provisional application No. 63/444,522, filed on Feb. 9, 2023.

(51) Int. Cl.
*G06T 5/50* (2006.01)
*G01N 21/31* (2006.01)
(Continued)

(52) U.S. Cl.
CPC .............. *G06T 5/50* (2013.01); *G01N 21/31* (2013.01); *G01N 33/4833* (2013.01); (Continued)

(58) Field of Classification Search
CPC ..................... G06T 5/50; G06T 7/0012; G06T 2207/10016; G06T 2207/10024; (Continued)

(56) References Cited

U.S. PATENT DOCUMENTS 12,133,762 B2 * 11/2024 Klingensmith ........... G06T 7/75

FOREIGN PATENT DOCUMENTS

WO WO-2023205631 A2 * 10/2023 ......... A61B 1/00165
WO WO-2025144823 A1 * 7/2025 ............. G06V 20/10

OTHER PUBLICATIONS

French et al., "Speckle-based hyperspectral imaging combining multiple scattering and compressive sensing in nanowire mats," Optics Letters 42, 1820-1823, 9, (2017).
(Continued)

*Primary Examiner* — Charlotte M Baker

(74) *Attorney, Agent, or Firm* — Piroozi-IP, LLC

(57) ABSTRACT

A method of generating an image or video of a field of interest of a sample which includes obtaining i) a first RGB image from a field of interest of a sample, and ii) hyperspectral data from a subarea of the field of interest, extracting an RGB image of the subarea from the first RGB image of the field of interest, applying the hyperspectral data of the subarea to conduct a spectroscopic analysis of a sample thereby generating spectral parameters, inputting i) the spectral parameters, and ii) the first RGB image, collectively as training input data to a deep learning model (DLM), training the DLM with the training input data thus generating a trained DLM, obtaining and inputting a second RGB image of about the field of interest to the trained DLM, and outputting from the trained DLM a spectral map for the field of interest.

20 Claims, 10 Drawing Sheets
(9 of 10 Drawing Sheet(s) Filed in Color)

FIG. 2

(51) Int. Cl.
| | | |
|---|---|---|
| *G01N 33/483* | (2006.01) | |
| *G06T 7/00* | (2017.01) | |
| *H04N 23/10* | (2023.01) | |

(52) U.S. Cl.
CPC ........... *G06T 7/0012* (2013.01); *H04N 23/10* (2023.01); *G06T 2207/10016* (2013.01); *G06T 2207/10024* (2013.01); *G06T 2207/10056* (2013.01); *G06T 2207/20081* (2013.01); *G06T 2207/20084* (2013.01); *G06T 2207/30024* (2013.01)

(58) Field of Classification Search
CPC . G06T 2207/10056; G06T 2207/20081; G06T 2207/20084; G06T 2207/30024; G06T 7/0016; G06T 2207/30104; G01N 21/31; G01N 33/4833; H04N 23/10
USPC ......................................................... 382/156
See application file for complete search history.

(56) References Cited

OTHER PUBLICATIONS

Deng et al., "Snapshot hyperspectral imaging via spectral basis multiplexing in Fourier domain," Optics Express 26, 32509-32521, 25, (2018).
Antipa et al., "DiffuserCam: Lensless single-exposure 3D imaging," Optica 5, 1-9, 1, (2018).
Wang et al., "HyperReconNet: Joint coded aperture optimization and image reconstruction for compressive hyperspectral imaging," IEEE Transactions on Image Processing 28, 2257-2270, 5, (2019).
Toivonen et al., "Snapshot hyperspectral imaging using wide dilation networks," Machine Vision and Applications 32, 1, (2020).
Bacca et al., "Compressive spectral image reconstruction using deep prior and low-rank tensor representation," Applied Optics 60, 4197-4207, 14, (2021).
Lin et al., "Dual-modality endoscopic probe for tissue surface shape reconstruction and hyperspectral imaging enabled by deep neural networks," Medical Image Analysis 48, 162, (2021).
Brown et al., "Neural network-based on-chip spectroscopy using a scalable plasmonic encoder," ACS Nano 15, 6305-6315, 4, (2021).
Kudenov et al., "Practical spectral photography II: Snapshot spectral imaging using linear retarders and microgrid polarization cameras," Optics Express 30, 12337-12352, 8, (2022).
Xie et al., "Dual camera snapshot hyperspectral imaging system via physics-informed learning," Optics and Lasers in Engineering 154, (2022).
Xiong et al., "Dynamic brain spectrum acquired by a real-time ultraspectral imaging chip with reconfigurable metasurfaces," Optica 9, 461-468, 5, (2022).
Lu et al., "Medical hyperspectral imaging: A review," Journal of Biomedical Optics 19, 1, (2014).
Pichette et al., "Intraoperative video-rate hemodynamic response assessment in human cortex using snapshot hyperspectral optical imaging," Neurophotonics 3, 045003, 4, (2016).
Mori et al., "Intraoperative visualization of cerebral oxygenation using hyperspectral image data: A two-dimensional mapping method," International Journal of Computer Assisted Radiology and Surgery 9, 1059-1072, 6, (2014).
Chen et al., "Modified Wiener estimation of diffuse reflectance spectra from RGB values by the synthesis of new colors for tissue measurements," Journal of Biomedical Optics 17, 3, (2012).
Yoshida et al., "Multispectral imaging of absorption and scattering properties of in vivo exposed rat brain using a digital red-green-blue camera," Journal of Biomedical Optics 20, 5, (2015).
Yoon et al., "Hyperspectral imaging using RGB color for foodborne pathogen detection," Journal of Electronic Imaging 24, 4, (2015).
Galliani et al., Learned spectral super-resolution, arXiv preprint arXiv:1703.09470, (2017).
Koundinya et al., "2D-3D CNN based architectures for spectral reconstruction from RGB images," IEEE/CVF Conference on Computer Vision and Pattern Recognition Workshops (CVPRW), 957-964, (2018).
Khansari et al., "Inter-visit variability of conjunctival microvascular hemodynamic measurements in healthy and diabetic retinopathy subjects," Microvascular Research 118, 7-11, (2018).
Watanabe et al., "Hemoglobin phase of oxygenation and deoxygenation in early brain development measured using fNIRS," National Academy of Sciences of the United States of America 114, E1737-E1744, 9, (2017).
Liang et al., "Symbolic time series analysis of fNIRS signals in brain development assessment," Journal of Neural Engineering 15, 6, (2018).
Zhang, "Film-like images with super-fine details using Foveon X3 Technology," Imaging Systems and Applications, IM3E. 4, (2017).
Zhao et al., "Perfect RGB-IR color routers for sub-wavelength size CMOS image sensor pixels," Advanced Photonics Research 2, 2000048, 3, (2021).
Zou et al., "Pixel-level Bayer-type colour router based on metasurfaces," Nature Communications 13, 1-7, 1, (2022).
Royle et al., "Parental investment and egg yolk lipid composition in gulls," Functional Ecology 13, 298-306, 3, (1999).
Van Veen et al., "Determination of visible near-IR absorption coefficients of mammalian fat using time- and spatially resolved diffuse reflectance and transmission spectroscopy," Journal of Biomedical Optics 10, 054004, 5, (2005).
Lagarias et al., "Convergence properties of the Nelder-Mead simplex method in low dimensions," SIAM Journal on Optimization 9, 112-147, 1, (1998).
Kruse et al., "The Spectral Image-Processing System (Sips)—Interactive visualization and analysis of imaging spectrometer data," Remote Sensing of Environment 44, 145-163, 2-3, (1993).
Arrieta et al., "Explainable Artificial Intelligence (XAI): Concepts, taxonomies, opportunities and challenges toward responsible AI," Information Fusion 58, 82-115, (2020).
Karniadakis et al., "Physics-informed machine learning," Nature Reviews Physics 3, 422-440, 6, (2021).
Cuomo et al., "Scientific machine learning through physics-informed neural networks: Where we are and what's next," Journal of Scientific Computing 92, 3, (2022).
Skopal et al., "Early evolution of the extraordinary Nova Delphini 2013 (V339 Del)," Astronomy & Astrophysics 569, A112, (2014).
Finlayson et al., "Rank-based camera spectral sensitivity estimation," Journal of the Optical Society of America A 33, 589-599, 4, (2016).
Ji et al., "Compressive recovery of smartphone RGB spectral sensitivity functions," Optics Express 29, 11947-11961, 8, (2021).
Finlayson et al., "Finding a colour filter to make a camera colorimetric by optimisation," Computational Color Imaging 11418, 53-62, (2019).
Yoon et al., "Hyperspectral image recovery using a color camera for detecting colonies of foodborne pathogens on agar plate," Journal of Biosystems Engineering 44, 169-185, 3, (2019).
Flock et al., "Monte Carlo modeling of light-propagation in highly scattering tissues. 1. Model predictions and comparison with diffusion-theory," IEEE Transactions on Biomedical Engineering 36, 1162-1168, 12, (1989).
Finlay et al., "Effect of pigment packaging on diffuse reflectance spectroscopy of samples containing red blood cells," Optics Letters 29, 965-967, 9, (2004).
Amelink et al., "Confidence intervals on fit parameters derived from optical reflectance spectroscopy measurements," Journal of Biomedical Optics 13, 5, (2008).
Rajaram et al., "Experimental validation of the effects of microvasculature pigment packaging on in vivo diffuse reflectance spectroscopy," Lasers in Surgery and Medicine 42, 680-688, 7, (2010).
Boas et al., Handbook of biomedical optics, p. 787 (CRC Press, Boca Raton, 2011).
Simonyan et al., "Deep inside convolutional networks: Visualising image classification models and saliency maps," arXiv preprint arXiv:1312.6034, (2013).

(56)                    References Cited

OTHER PUBLICATIONS

Selvaraju et al., "Grad-cam: Visual explanations from deep networks via gradient-based localization," IEEE International Conference on Computer Vision, 618-626, (2017).

Perry, "A complete culture system for the chick-embryo," Nature 331, 70-72, 6151, (1988).

Yoon et al., "A background correction method to compensate illumination variation in hyperspectral imaging," Plos One 15, 3, (2020).

Abraham et al., "Continuous monitoring of tissue pH with a fiberoptic conjunctival sensor," Annals of Emergency Medicine 14, 840-844, 9, (1985).

Lin et al., "Melanocyte biology and skin pigmentation," Nature 445, 843-850, 7130, (2007).

Yan et al., "Accurate spectral super-resolution from single RGB image using multi-scale CNN," Pattern Recognition and Computer Vision 11257, 206-217, (2018).

Stiebel et al., "Reconstructing spectral images from RGB-images using a convolutional neural network," IEEE/CVF Conference on Computer Vision and Pattern Recognition Workshops (CVPRW), 1061-1066, (2018).

Arad et al., "NTIRE 2018 challenge on spectral reconstruction from RGB images," IEEE/CVF Conference on Computer Vision and Pattern Recognition Workshops (CVPRW), 1042-1051, (2018).

Kaya et al., "Towards spectral estimation from a single RGB image in the wild," IEEE/CVF International Conference on Computer Vision Workshops (ICCVW), 3546-3555, (2019).

Park et al., "mHealth spectroscopy of blood hemoglobin with spectral super-resolution," Optica 7, 563-573, 6, (2020).

Zou et al., "Cluster-based deep convolutional networks for spectral reconstruction from RGB images," Neurocomputing 464, 342-351, (2021).

Lin et al., "Physically plausible spectral reconstruction from RGB Images," IEEE/CVF Conference on Computer Vision and Pattern Recognition Workshops (CVPRW), 2257-2266, (2020).

Kwak et al., "A pearl spectrometer," Nano Letters 21, 921-930, 2, (2021).

Lin et al., "On the optimization of regression-based spectral reconstruction," Sensors 21, 16, (2021).

Arad et al., "NTIRE 2020 challenge on spectral reconstruction from an RGB image," IEEE/CVF Conference on Computer Vision and Pattern Recognition Workshops (CVPRW), 1806-1822, (2020).

Munos et al., "Mobile health: The power of wearables, sensors, and apps to transform clinical trials," Annals of the New York Academy of Sciences 1375, 3-18, Special Issue: Annals Reports, (2016).

Wood et al., "Taking connected mobile-health diagnostics of infectious diseases to the field," Nature 566, 467-474, 7745, (2019).

Mathews et al., "Digital health: A path to validation," npj Digital Medicine 2, 1-9, (2019).

Hunt et al., "Smartphone-based imaging systems for medical applications: A critical review," Journal of Biomedical Optics 26, 4, (2021).

Hussain et al., "Smartphone-based optical spectroscopic platforms for biomedical applications: A review," Biomedical Optics Express 12, 1974-1998, 4, (2021).

Hussain et al., "A multi-channel smartphone-based spectroscopic system for high-throughput biosensing in low-resource settings," Analyst 147, 3007-3016, 13, (2022).

Sedhom et al., "Mobile app validation: A digital health scorecard approach," npj Digital Medicine 4, 1, (2021).

Von Rueden et al., "Informed machine learning—A taxonomy and survey of integrating knowledge into learning systems," arXiv preprint arXiv:1903.12394, (2019).

Iten et al., "Discovering physical concepts with neural networks," Physical Review Letters 124, 1, (2020).

Zhang et al., "Deeply learned broadband encoding stochastic hyperspectral imaging," Light-Science & Applications 10, 1, (2021).

Sun et al., "pHSCNN: CNN-based hyperspectral recovery from a pair of RGB images," Optics Express 30, 24862-24873, 14, (2022).

Du et al., Label-free hyperspectral imaging and deep-learning prediction of retinal amyloid β-protein and phosphorylated tau, PNAS nexus 1, 164, 4, (2022).

Wei et al., "Fast fusion of multi-band images based on solving a Sylvester equation," IEEE Transactions on Image Processing 24, 4109-4121, 11, (2015).

Kanatsoulis et al., "Hyperspectral super-resolution: A coupled tensor factorization approach," IEEE Transactions on Signal Processing 66, 6503-6517, 24, (2018).

Li et al., "Hyperspectral image super-resolution using deep convolutional neural network," Neurocomputing 266, 29-41, (2017).

Wang et al., Single-shot on-chip spectral sensors based on photonic crystal slabs, Nature Communications 10, 1-6, (2019).

Wang et al., "Snapshot channeled imaging spectrometer using geometric phase holograms," Optics Express 27, 15444-15455, 11, (2019).

He et al., "Analysis of skin morphological features and real-time monitoring using snapshot hyperspectral imaging," Biomedical Optics Express 10, 5625-5638, 11, (2019).

McClung et al., "Snapshot spectral imaging with parallel metasystems," Science Advances 6, 38, (2020).

Altaqui et al., "Mantis shrimp-inspired organic photodetector for simultaneous hyperspectral and polarimetric imaging," Science Advances 7, 10, (2021).

Monakhova et al., "Spectral DiffuserCam: Lensless snapshot hyperspectral imaging with a spectral filter array," Optica 7, 1298-1307, 10, (2020).

Yako et al., "Video-rate hyperspectral camera based on a CMOS-compatible random array of Fabry-Pérot filters," Nature Photonics, (2023).

Bouchard et al., "Ultra-fast multispectral optical imaging of cortical oxygenation, blood flow, and intracellular calcium dynamics," Optics Express 17, 15670-15678, 18, (2009).

He et al., "Hyperspectral imaging enabled by an unmodified smartphone for analyzing skin morphological features and monitoring hemodynamics," Biomedical optics express 11, 895-910, 2, (2020).

Johnson et al., "Snapshot hyperspectral imaging in ophthalmology," Journal of Biomedical Optics 12, 1, (2007).

Boniface et al., "Rapid broadband characterization of scattering medium using hyperspectral imaging," Optica 6, 274-279, 3, (2019).

Mu et al., "Snapshot hyperspectral imaging polarimetry with full spectropolarimetric resolution," Optics and Lasers in Engineering 148, 106767, (2022).

Wagadarikar et al., "Video rate spectral imaging using a coded aperture snapshot spectral imager," Optics Express 17, 6368-6388, 8, (2009).

Yokoya et al., "Hyperspectral and multispectral data fusion: A comparative review of the recent literature," IEEE Geoscience and Remote Sensing Magazine 5, 29-56, 2, (2017).

Huang et al., "Spectral imaging with deep learning," Light-Science & Applications 11, 1, (2022).

Yang et al., "Miniaturization of optical spectrometers," Science 371, 480, 6528, (2021).

Redding et al., "Compact spectrometer based on a disordered photonic chip," Nature Photonics 7, 746-751, 9, (2013).

Bao et al., "A colloidal quantum dot spectrometer," Nature 523, 67, 7558, (2015).

Ghamisi et al., "Advances in hyperspectral image and signal processing: A comprehensive overview of the state of the art," IEEE Geoscience and Remote Sensing Magazine 5, 37-78, 4, (2017).

Khan et al., "Modern trends in hyperspectral image analysis: A Review," IEEE Access 6, 14118-14129, (2018).

Yang et al., "Single-nanowire spectrometers," Science 365, 1017, 6457, (2019).

Jaiswal et al., "Critical insights into modern hyperspectral image applications through deep learning," Wiley Interdisciplinary Reviews-Data Mining and Knowledge Discovery 11, 6, (2021).

Reichstein et al., "Deep learning and process understanding for data-driven earth system science," Nature 566, 195-204, 7743, (2019).

Manifold et al., "A versatile deep learning architecture for classification and label-free prediction of hyperspectral images," Nature Machine Intelligence 3, 306, 4, (2021).

(56)                References Cited

OTHER PUBLICATIONS

Zhang et al., "A survey on computational spectral reconstruction methods from RGB to hyperspectral imaging," Scientific Reports 12, 11905, 1, (2022).

Tsagkatakis et al., "Survey of deep-learning approaches for remote sensing observation enhancement," Sensors 19, 3929, 18, (2019).

Hong et al., "Interpretable hyperspectral artificial intelligence: When nonconvex modeling meets hyperspectral remote sensing," IEEE Geoscience and Remote Sensing Magazine 9, 52-87, 2, (2021).

Kirchner et al., "Snapshot hyperspectral imaging (SHI) for revealing irreversible and heterogeneous plasmonic processes," Journal of Physical Chemistry C 122, 6865-6875, 12, (2018).

Hadoux et al., "Non-invasive in vivo hyperspectral imaging of the retina for potential biomarker use in Alzheimer's disease," Nature Communications 10, 1-12, (2019).

Yoon et al., "A clinically translatable hyperspectral endoscopy (HySE) system for imaging the gastrointestinal tract," Nature Communications 10, 1-13, (2019).

Zhang et al., "Unsupervised adaptation learning for hyperspectral imagery super-resolution," IEEE/CVF Conference on Computer Vision and Pattern Recognition (CVPR), 3070-3079, (2020).

Wang et al., "DNU: Deep non-local unrolling for computational spectral imaging," IEEE/CVF Conference on Computer Vision and Pattern Recognition (CVPR), 1658-1668, (2020).

* cited by examiner

| Training option | Property |
| --- | --- |
| Algorithm | Root mean square propagation (Adam) |
| Initial learning rate | 0.01 |
| Number of epochs | 50 |
| Mini-batch size | 20 |
| Learning rate drop period | 3 |
| L2 regularization factor | 0.00001 |

FIG. 4B

Oxyhemoglobin
RGB value

Deoxyhemoglobin
RGB value

HYPERSPECTRAL LEARNING FOR INSTANTANEOUS SPATIOSPECTRAL IMAGING OF HEMODYNAMICS

CROSS-REFERENCE TO RELATED APPLICATIONS

The present non-provisional patent application is related to and claims the priority benefit of U.S. Provisional Patent Application Ser. 63/444,522, filed Feb. 9, 2023, the contents of which are hereby incorporated by reference in its entirety into the present disclosure.

STATEMENT REGARDING GOVERNMENT FUNDING

This invention was made with government support under contract number TW012486 awarded by the National Institutes of Health. The government has certain rights in the invention.

TECHNICAL FIELD

The present disclosure generally relates to systems and methods related to imaging and in particular with regards to spatiospectral imaging of hemodynamics.

BACKGROUND

This section introduces aspects that may help facilitate a better understanding of the disclosure. Accordingly, these statements are to be read in this light and are not to be understood as admissions about what is or is not prior art.

Hyperspectral (with a high spectral resolution of ~10 nm) or multispectral (with several spectral bands of ~50 nm) imaging systems acquire a hyperspectral image dataset (hypercube)—a three-dimensional dataset of spectral intensity in spatial coordinates. Both spatial and spectral data are processed. Hyperspectral imaging technologies offer extensive physical and biological information in stationary or dynamic samples, ranging from microscopic settings to airborne remote-sensing environments, for a variety of applications in geology, mineralogy, agriculture, environmental science, astronomy, forensic medicine, defense, security, and biomedicine. Notably, hyperspectral imaging technologies have been reinvigorated through recent advances in data-driven machine learning. For example, deep-learning approaches have enabled the effective processing of extremely large hypercube data for classical imaging tasks and allowed for the optimization of hypercube acquisition to achieve specific tasks and objectives. Data fusion of complementary images with high-spectral or high-spatial resolutions and neural networks of improving spatial resolutions can overcome the intrinsic trade-off between spatial and spectral resolutions. However, conventional hyperspectral imaging systems still face the intrinsic limitations: bulky instruments, slow data acquisition rates, low detection efficacy (i.e., low signal-to-noise ratio), and motion artifacts.

Typically, hyperspectral imaging systems rely on mechanical scanning elements either in the spectral or spatial domains. In particular, spectral scanning systems employ a number of narrow bandpass spectral filters or dispersive optical components, whereas point scanning and line-scanning systems rely on mechanical translational components that require high precision. Thus, these scanning elements result in bulky instruments and yield suboptimal temporal resolutions. In particular, prolonged time of data acquisition time fundamentally limits dynamic imaging with a high temporal resolution. In this respect, the development of snapshot imaging technologies capable of acquiring a hypercube in a single shot manner has been an active area of research. The most common configuration used for snapshot imaging involves capturing multiple images with different spectral bands using a large-area image sensor. Specifically, large-area image sensor-based snapshot imaging is beneficial for reducing the acquisition time. Other snapshot-imaging technologies employ dispersion patterns or coded apertures projecting irradiance mixed with spatial and spectral information to further enhance the light-collection efficiency and readout rate. Subsequently, the modulated projection comprising spatial and spectral information is reconstructed into a hypercube by utilizing computational algorithms such as compressed (or compressive) sensing, or Fourier transformation.

However, previously developed hyperspectral imaging technologies with a snapshot ability face several limitations. First, typical snapshot systems are limited by the intrinsic tradeoff that must be made between the spectral and spatial resolutions; that is, an improvement in spatial resolution causes a deterioration in the number of spectral bands, thereby compromising the spectral resolution or the spatial resolution (or imaging area). Second, snapshot imaging systems are sensitive to light conditions and imaging configurations, thereby introducing significant errors in field applications. Third, the hyperspectral filter arrays, dispersion patterns, and coded apertures require high-precision fabrication or nanofabrication, including precision alignment of array components, optimized miniaturization, integration with pixel-level filters, and customized calibrations, all of which inhibit manufacturability. Consequently, the previous studies have generally been performed under laboratory settings or with stationary biological samples, thereby hampering the practical and widespread utilization.

Therefore, there is an unmet need for a novel approach in instantaneous hyperspectral imaging that enables the recovery of spectral information from conventional equipment which can provide a full reflectance spectrum in the visible range.

SUMMARY

A method of generating an image or video of a field of interest of a sample is disclosed. The method includes obtaining i) a first Red-Green-Blue (RGB) image from a field of interest of a sample, and ii) hyperspectral data from a subarea of the field of interest. The method further includes extracting an RGB image of the subarea from the first RGB image of the field of interest, and applying the hyperspectral data of the subarea to conduct a spectroscopic analysis of a sample, thereby generating spectral parameters. The method also includes inputting i) the spectral parameters, and ii) the first RGB image, collectively as training input data to a deep learning model, and training the deep learning model with the training input data thus generating a trained deep learning model. Additionally, the method includes obtaining a second RGB image about the field of interest including areas outside of the subarea; inputting the second RGB image of the field of interest to the trained deep learning model, and outputting from the trained deep learning model a spectral map for the field of interest.

BRIEF DESCRIPTION OF FIGURES

The patent or application file contains at least one drawing executed in color. Copies of this patent or patent application publication with color drawing(s) will be provided by the Office upon request and payment of the necessary fee.

FIGS. 4A and 4B are i) an architecture diagram (FIG. 4A), according to the present disclosure, and ii) key hyperparameters (FIG. 4B) of the deep neural network that directly return the hemodynamic parameters of Hb and $HbO_2$ from RGB input values.

DETAILED DESCRIPTION

Figures 1, 2:
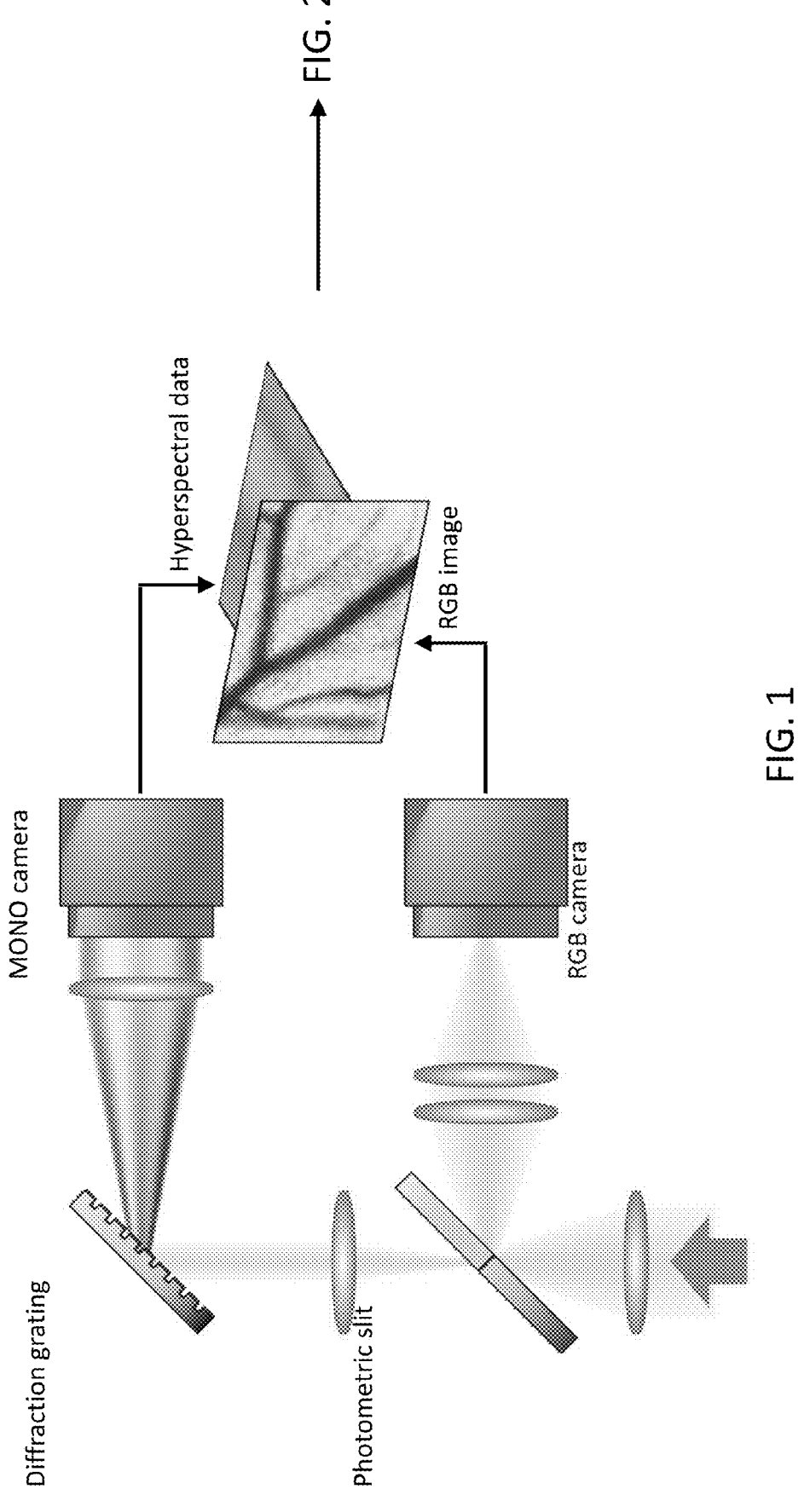
FIG. 1 is a schematic of an experimental setup according to the present disclosure including a trichromatic Red-Green-Blue (RGB) camera (e.g., a smartphone camera) and a spectrograph camera.
FIG. 2 is a block diagram that outlines the steps of the approach provided in the present disclosure.
Figure 2:
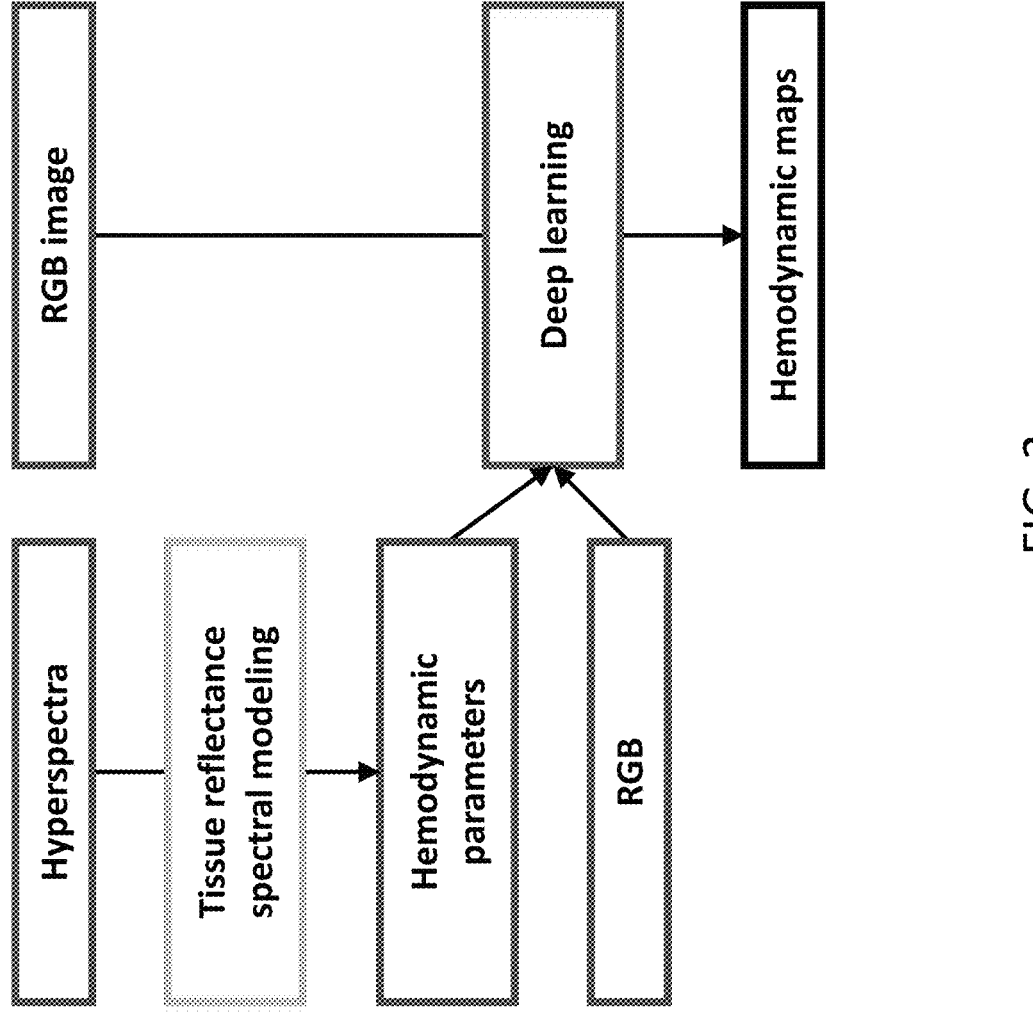

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel approach in instantaneous hyperspectral imaging is disclosed herein that enables the recovery of spectral information from conventional equipment which can provide a full reflectance spectrum in the visible range. Towards this end, a deep learning approach is disclosed herein which enables the recovery of spectral information from Red-Green-Blue (RGB) values acquired by a conventional trichromatic camera in order to generate a full reflectance spectrum in the visible range via computational reconstruction from an RGB image. Owing to its hardware simplicity, the disclosed novel approach can be performed by using a smartphone camera without the need for complex equipment add-ons such as dispersive optical components, e.g., spectrometers and bulky optical filters.

The disclosed novel approach includes a learning-based spatiospectral imaging method offering high spectral and temporal resolutions. The disclosed spectral learning involves mapping from a sparse spectral space (i.e., RGB values) to a dense spectral space. Specifically, the spectral resolution is in a range of 0.5-1 nm, comparable to those of scientific spectrometers and spectrographs for biomedical or biochemical applications (thereby referred to as hyperspectral learning, compared with spectral learning). First, we construct a customized dual-channel imaging setup coupled with a trichromatic camera (e.g., smartphone camera) and a spectrograph to acquire an RGB image and subarea hyperspectral data. Second, we establish a simple statistical assumption to infer the entire field-of-view from a sampled subarea and recover a hypercube from incomplete measurements. Third, we establish a machine-learning frameworks based on deep learning, incorporating the domain knowledge of tissue optics into learning algorithms. Finally, we demonstrate reliable extractions of hemodynamic parameters from several different samples of tissue phantoms, chick embryos, and human conjunctiva; the results are validated through conventional hyperspectral imaging and functional near-infrared spectroscopy. Moreover, this hyperspectral learning method is applied to smartphone video recording to demonstrate the dynamic imaging of peripheral microcirculation and ultrafast imaging of oxygen depletion in tissue phantoms.

Referring to FIG. 1, an experimental setup is shown including a trichromatic RGB camera (e.g., a smartphone camera) and a spectrograph camera. Light from a sample is passed through a lens and shone upon a photometric slit which acts both as a mirror allowing visibility to the entire sample area via one or more lenses that focus light onto the RGB camera, thus allowing the RGB camera to obtain an RGB image of the entire sample area. Additionally, the photometric slit provides a slit through which light propagates onto a lens and which is shone onto a diffraction grating causing light to be dispersed into a plurality of bandwidths (i.e., different colors). The diffracted light then passes through a lens and onto the spectrograph camera which can obtain hyperspectral data from a limited portion of the sample area dictated by the slit. The position of the slit determines which limited portion of the sample area is captured by the spectrograph camera. In FIG. 1, the slit is positioned such that the hyperspectral data is of a plane that is situated about the center of the sample viewing area as captured by the RGB camera.

FIG. 1, thus illustrates the concept of hyperspectral learning for instantaneous spatiospectral imaging by significantly minimizing the number of necessary hyperspectral measurements. If hyperspectral data in a small yet representative subarea are available, a hyperspectral learning algorithm can be trained using the RGB and hyperspectral data in the subarea. This hyperspectral learning algorithm trained by the sampled (RGB and hyperspectral) data is applied to the entire image area, generating a hypercube without the need for a complete spectral or spatial scan. Thus, the key advantages of hyperspectral learning and hypercube recovery include the hardware simplicity offered by the use of conventional cameras, high temporal resolution if a video is used (e.g., slow-motion video recording on a smartphone), independence (no tradeoff) between the spatial and spectral resolutions, and abundant spectral information for a variety of machine-learning techniques. Locally sampled hyperspectral data can serve as prior information or physical constraints for incorporating domain-specific modeling into the learning algorithm, extracting critical features and parameters, and resulting in explainable and interpretable neural networks.

To instantaneously sample hyperspectral data in a small subarea, the trichromatic camera (e.g., smartphone camera) is combined with a line-scan spectrograph. Specifically, a dual-channel spectrograph with a photometric slit acquires an RGB image in the entire area and the hyperspectral data of a subarea (e.g., a central line) in a single-shot manner. The field-of-view may be as small as 2.5 mm×2 mm with a spatial resolution of 55 μm. The sampled hyperspectral data have a spectral range of λ=380-720 nm with a spectral resolution Δλ=0.5 nm. The dual-channel imaging setup provides sufficient training data (750-1500 data points) for the machine learning package (e.g., a neural network as further described in FIG. 2 and below). This dataset is randomly split into training (80%) and testing (20%) datasets for effectively training the hyperspectral learning algorithm to be applied to the entire area eventually (see FIG. 2). In addition, this imaging setup allows us to use a smartphone camera that can acquire videos at different frame rates. In particular, highly dynamic imaging is even possible with a high temporal resolution even up to 0.0005 sec for 1920 frames per second, using commercially available smartphone models.

Referring to FIG. 2, a block diagram is provided that outlines the steps of the present approach. Hyperspectral data from the slit is provided to a model of interest. For example, if hemodynamic parameters are of interest, the model may be a tissue reflectance spectral model. The output of the model will include parameters of interest. In the case of hemodynamics, the model's output includes hemodynamic parameters. These output parameters along with the RGB image from the same limited area corresponding to the slit are provided as input to a deep learning modeling package along with the RGB of the entire sample area. The deep learning package then provides the hemodynamic parameters for the entire sample viewing area in the form of a hemodynamic map. It should be appreciated by tailoring the tissue reflectance spectral model to other parameters of interest, the deep learning package may be configured to output selective maps of the entire sample image area.

The hyperspectral learning addresses an ill-posed problem, which is also known as spectral super-resolution and hyperspectral reconstruction. The mathematical relationship between the RGB and hyperspectral intensity is provided as:

$$x_{3\times1} = S_{3\times k} y_{k\times1} + e_{3\times1} \qquad (1)$$

where x denotes a 3×1 vector corresponding to three color values in the R, G, and B channels $$(x = [R, G, B]^T),$$

S represents a 3×k matrix of the RGB spectral response of the three-color sensor the spectral response functions in the R, G, and B channels of the smartphone camera (also known as the sensitivity function of the camera), y is a k×1 vector that has the spectral intensity (y=[I(λ₁), I(λ₂), . . . , I(λₖ)]ᵀ) where A is discretized in the visible range with a spectral interval of 1 nm, and e symbolizes a 3×1 vector of the system noise. Thus, hyperspectral learning amounts to obtaining a pseudo-inverse of $S_{3\times k}$. Depending on the availability of training data and the desired spectral resolution, the machine-learning approach discussed herein is a deep learning approach using a neural network.

A key assumption for reliable hyperspectral learning is that a sampling distribution (i.e., RGB values of the sampled subarea) should follow the parent distribution (i.e., RGB values of the entire image area); i.e., the intensity distributions between the sampled subarea and the entire field-of-view of interest are about statistically the same. Specifically, the probability distribution of the R, G, and B values in the subarea needs to conform to those in the entire area in terms of variability and shape. In addition, to reliably predict unknown hyperspectral output responses from RGB values outside the subarea, the hyperspectral learning algorithm should be applied within the same (minimum and maximum) range of sampled RGB values used to train the algorithm. In a similar manner to nonparametric tests with non-Gaussian distributions, known to a person having ordinary skill in the art, quantile-quantile (Q-Q) plots can conveniently be used to assess if the two sets of data plausibly follow the same distribution within the same range. Validity of this assumption allows for interpolation from the subarea to the entire field which offers an important advantage over conventional snapshot hyperspectral imaging. If these assumptions are valid, then the hyperspectral learning is not limited by the intrinsic tradeoff between spatial and spectral resolutions.

This assumption can be tested and further optimized, by 1) changing the location of the subarea (i.e., position of the slit in FIG. 1), 2) dividing a frame into subframes, where the subframes each produce a more favorable assumption as compared to the entire frame, and 3) a combination of (1) and (2). These three methods can be combined with an optimization approach, e.g., least-squares, using a feedback signal in order to minimize error using a quantitative approach, e.g., Q-Q plots.

Spectrally informed learning allows for the incorporation of physical and biological understanding of domain knowledge into learning algorithms. Among the various snapshot imaging applications, we focus on extracting biological parameters or spectral signatures from a hypercube using the domain knowledge of tissue optics. In this perspective, light propagation in tissue can be explained by the theory of radiative transport and robust approximations (e.g., diffusion, Born, and empirical modeling). Specifically, taking advantage of tissue reflectance spectral modeling, we extract the key hemodynamic parameters: oxygenated hemoglobin (HbO₂), deoxygenated hemoglobin (Hb), and oxygen saturation (sPO₂), which are the fundamental determinants of oxygen transport to tissue associated with a variety of physiological changes, diseases, and disorders, as described below:

$$sPO2 = \frac{HbO_2}{\text{Total hemoglobin}} = \frac{HbO_2}{HbO_2 + Hb} \qquad (2)$$

Notably, tissue optics serves as the cornerstone of biophotonics and biomedical optics to deepen our knowledge of light-tissue interactions and develop noninvasive optical diagnostic methods and devices. Typically, purely data-driven learning requires a large volume of training data and lacks explainable and interpretable learning. On the other hand, tissue optics modeling can offer insights into the black box nature of deep learning.

To demonstrate the versatility of hyperspectral learning and hypercube recovery, we formulate a deep learning approach (see FIG. 2), where hyperspectral data in a subarea is directly fed into the tissue reflectance spectral model to compute the hemodynamic parameters within the same subarea. The obtained dataset serves to train a deep neural network that computes the hemodynamic parameters with RGB values (tristimulus) as an input. Specifically, the deep neural network is directly trained by using the hemodynamic parameters extracted from the tissue reflectance spectral model fed with the sampled data, thereby reducing the computational load. In both cases, separate training and validation datasets are employed to strengthen the learning algorithm for training: 80% of the data points among the sampled data (i.e., 600 data points out of 750) are randomly selected as a training dataset and the remaining 20% (i.e., 150 data points) are blindly tested as a testing dataset.

Figure 3:
FIG. 3 is a schematic representing a conceptual illustration of a deep neural network that receives RGB values and returns key hemodynamic parameters (e.g., Hb and $HbO_2$).
Figure 4A:
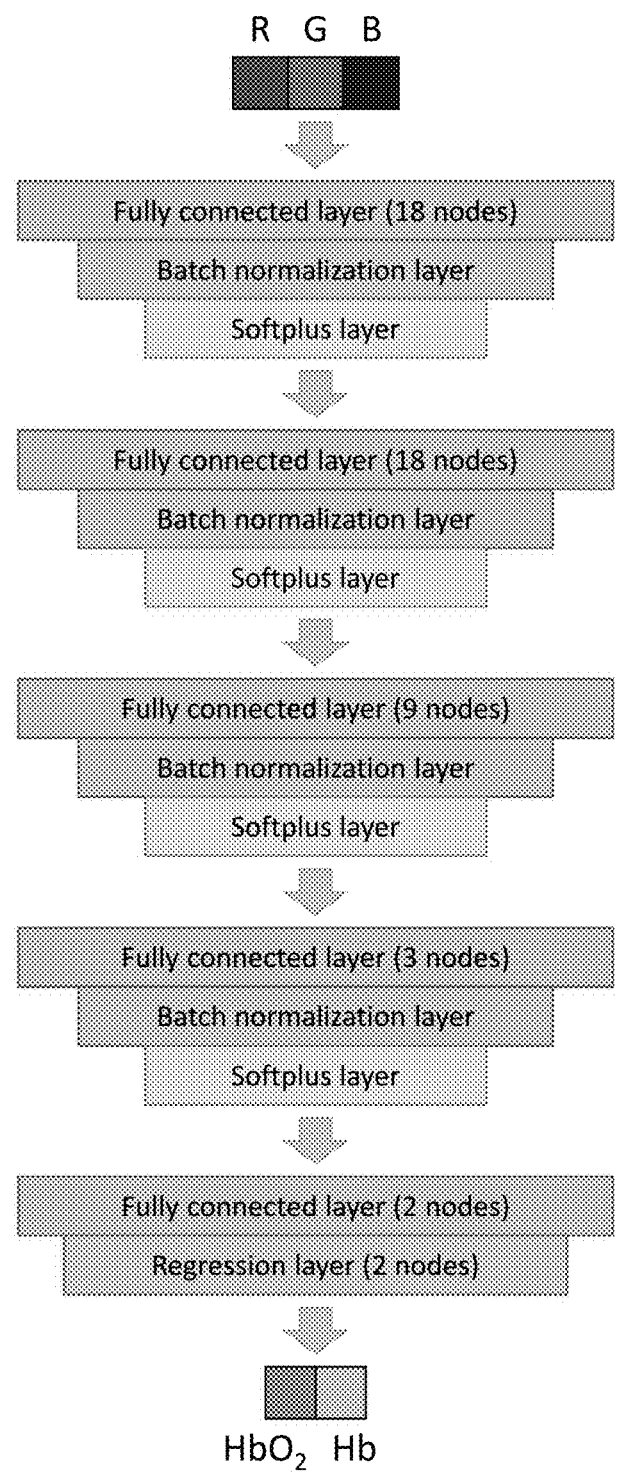
Figure 5:
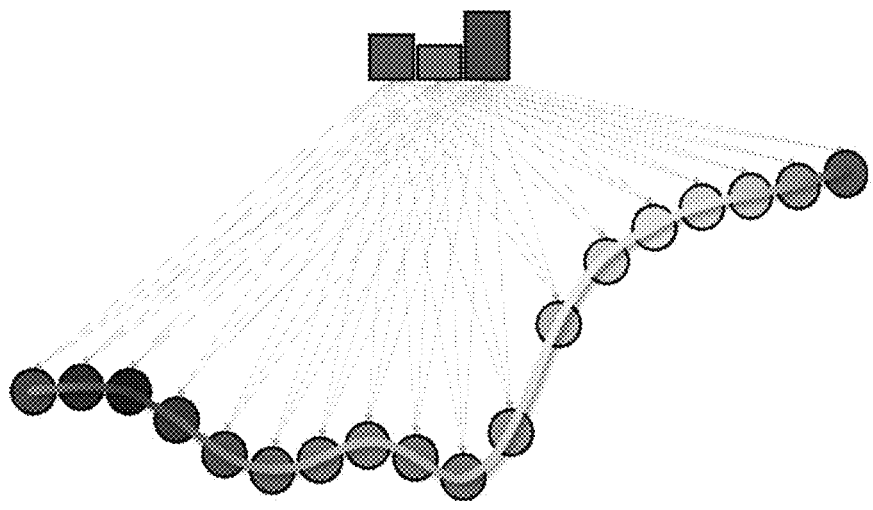
FIG. 5 is a schematic representing the first hidden layer of a deep neural network which is fully connected to 18 nodes (or neurons).
Figure 5:
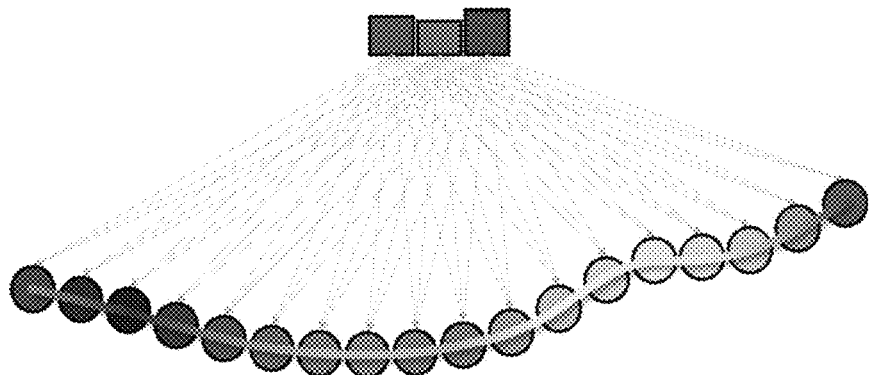
Figure 6B:
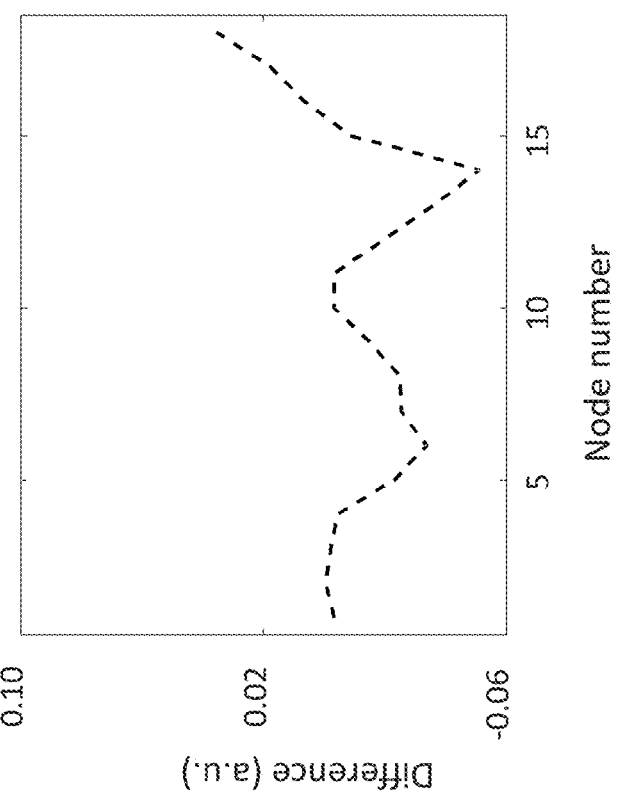
FIG. 6B is a graph of spectral intensity differences vs. wavelength representing difference in the computed output values of the first hidden layer between two different RGB values of $HbO_2$ and Hb from the same tissue phantom in FIG. 6A.
Figure 6A:
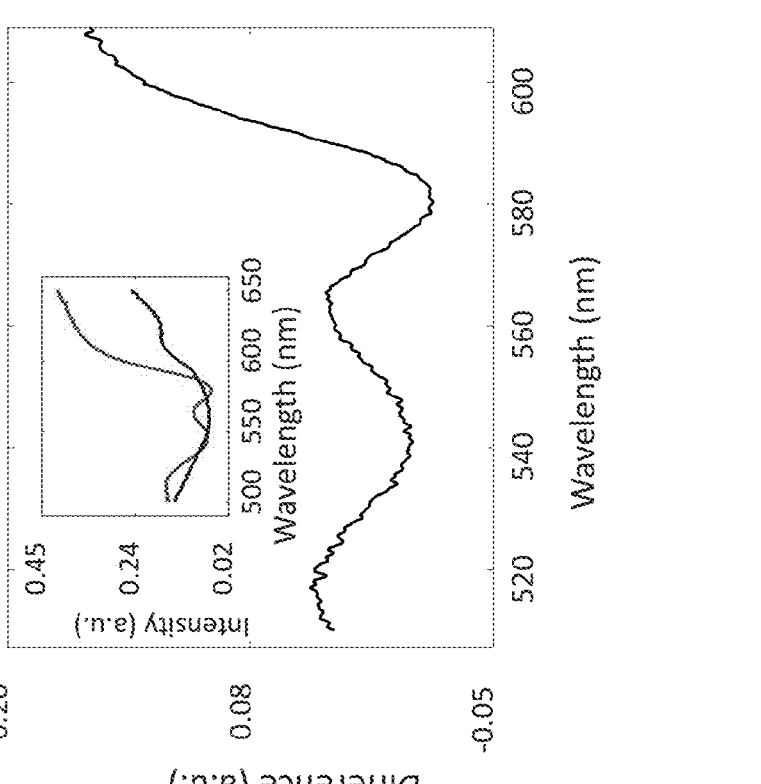
FIG. 6A is a graph of spectral intensity differences vs. wavelength representing spectral intensity differences in hyperspectral data measured from a tissue phantom with oxygenated and deoxygenated hemoglobin.

Importantly, deep learning informed by hyperspectral information is advantageous for designing explainable and interpretable neural networks. Among similar yet distinct terms, such as understandability and comprehensibility, spectrally informed deep learning enables transparency in the learning algorithm as it is understandable in a manner similar to statistical regression. A conceptual drawing of the neural network is shown in FIG. 3 (a conceptual illustration of the deep neural network that receives RGB values and returns key hemodynamic parameters (i.e., $HbO_2$ and Hb). This network is trained by the RGB values and hemodynamic parameters in a subarea; $HbO_2$ and Hb values are computed from the measured hyperspectral data in the subarea via the tissue reflectance spectral model), with more information provided in FIGS. 4A and 4B. Specifically, FIGS. 4A and 4B provide architecture diagram and key hyperparameters of the deep neural network that directly returns the hemodynamic parameters of Hb and $HbO_2$ from the RGB input values. Specifically, in FIG. 4A the network is informed by hyperspectral learning as well as tissue reflectance spectral modeling such that the output hemodynamic parameters are extracted from tissue reflectance spectral modeling. FIG. 4B provides training options and hyperparameters that are optimized to efficiently extract the hemodynamic parameters directly from the RGB values. The first hidden layer, which is one of the important hyperparameters for building a neural network, is fully connected with a relatively large number of nodes (e.g., 18 nodes), which transforms RGB values to a spectral intensity profile with a high spectral resolution. After the network is trained, each node in the first hidden layer possesses a distinct weight representing hyperspectral information, such that the RGB values of a certain hemodynamic parameter (e.g., $sPO_2$) generate the corresponding spectral feature, which is further propagated throughout the network as shown in FIG. 5 (the first hidden layer is fully connected to 18 nodes (or neurons)). FIG. 6A illustrates two representative cases of hyperspectral data measured from a tissue phantom by varying $sPO_2$ between $HbO_2$ and Hb. The output values at different nodes in the first hidden layer can be understood based on the spectral intensity differences as a function of $\lambda$ (see FIGS. 6A and 6B) that a scientific spectrometer or spectrograph can quantify. FIG. 6A is a representative spectral intensity differences in hyperspectral data measured from a tissue phantom with oxygenated and deoxygenated hemoglobin. Inset: represents measured hyperspectral data when the sample is oxygenated (red curve) and deoxygenated (blue curve) (i.e., $HbO_2$ or Hb, respectively). FIG. 6B is a representative difference in the computed output values of the first hidden layer between two different RGB values of $HbO_2$ and Hb from the same tissue phantom in FIG. 6A. The order of the nodes is assigned such that the rank of the output differences is the same as that of the wavelengths in the spectral intensity differences. This direct spectral understanding should be differentiated from other conventional heatmaps or saliency maps employed for visualizing or explaining features extracted through typical convolutional neural networks. In particular, the differences in the computed output values of the first hidden layer between the two different RGB values of $HbO_2$ and Hb in a tissue phantom resemble the spectral intensity differences between $HbO_2$ and Hb measured from the same tissue phantom.

In the deep-learning framework (see FIG. 2), we design a fully connected deep neural network that takes RGB values as the input and returns the hemodynamic parameters as the output (see FIGS. 3 and 4A). As stated previously, the neural network incorporates the output parameters extracted from the tissue reflectance spectral modeling (see FIG. 5).

Figures 7A, 7B, 7C, 7D:
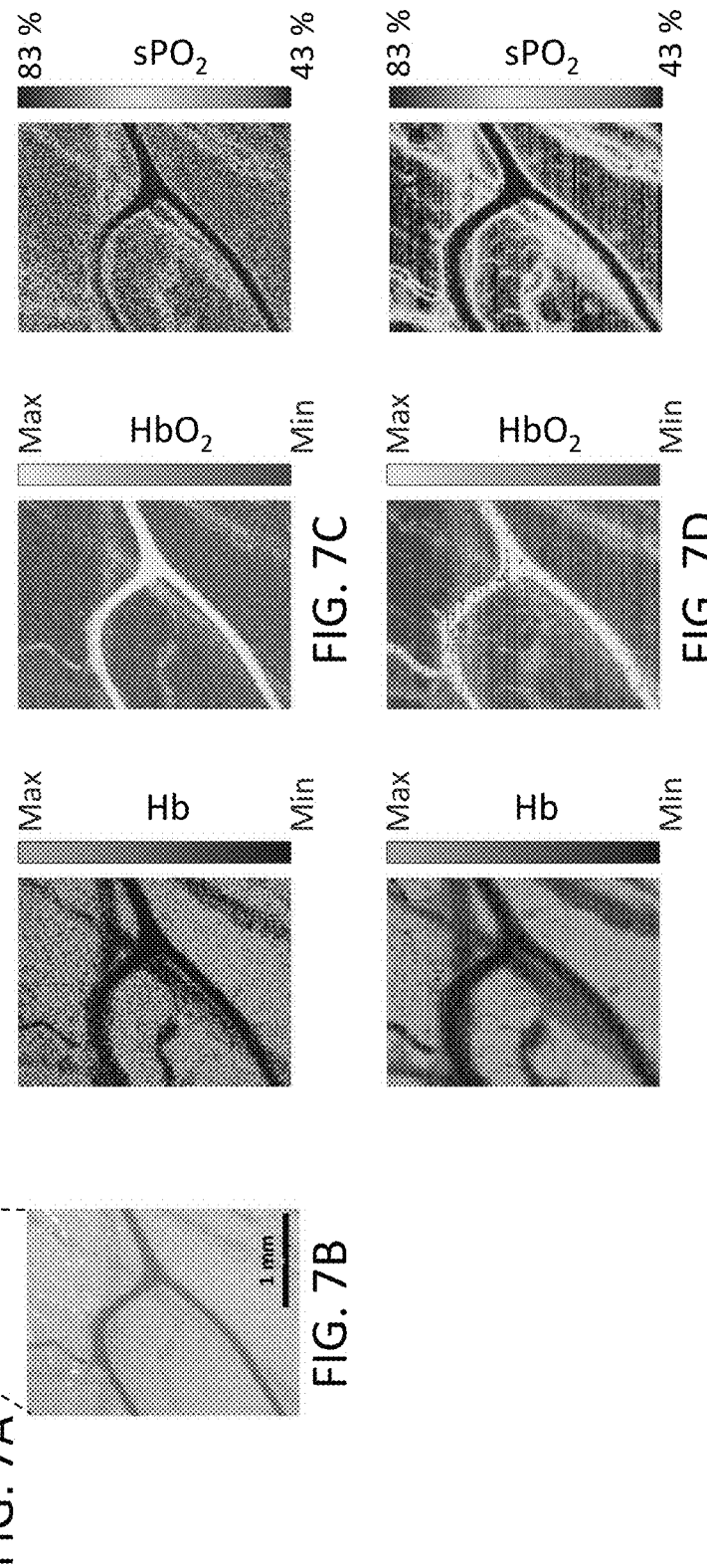
FIGS. 7A, 7B, 7C, and 7D are images of vascular tissue in a petri dish as an experimental vascular developmental model, wherein RGB images generated by the conventional pushbroom-type hyperspectral imaging system of the prior art are shown in FIGS. 7A and 7B, a ground truth for the hemodynamic map of Hb, $HbO_2$, and $sPO_2$ corresponding to a white leghorn chicken (*Gallus domesticus*, Hy-Line W-36) embryo on day 8 based on FIG. 7B (shown in FIG. 7C), and the deep learning-based hemodynamic maps are shown in FIG. 7D.

Referring to FIGS. 7A, 7B, 7C, and 7D, a chick embryo in a petri dish as an experimental vascular developmental model is shown in FIG. 7A. RGB image generated by the conventional pushbroom-type hyperspectral imaging system of the prior art is shown (FIG. 7B) and a ground truth for the hemodynamic map of Hb, $HbO_2$, and $sPO_2$ corresponding to a white leghorn chicken (*Gallus domesticus*, Hy-Line W-36) embryo on day 8 based on FIG. 7B is shown in FIG. 7C. The deep learning-based hemodynamic maps are shown in FIG. 7D. The hemodynamic maps (FIG. 7D) are directly generated using the deep neural network approach discussed herein that takes the RGB values as the input and returns $HbO_2$ and Hb values as the output. Reference hemodynamic maps that is generated by the conventional pushbroom-type hyperspectral imaging system used for validation is shown in FIG. 7C. The deep learning-neural network based hemodynamic map (FIG. 7D) is in excellent agreement with the ground-truth maps shown in FIG. 7C. Deep learning-based hemodynamic maps are further assessed using the structural similarity index to show that they are qualitatively identical to the reference hemodynamic maps as provided below. Interestingly, the conventional hemodynamic maps shown in FIG. 7C are noisier due to the motion artifact of the live sample, which results from the slow rate of data acquisition (data acquisition time=45 minutes) and the mechanical scanning, as shown by the horizontal lines in FIG. 7C.

TABLE 1

Structural similarity index values to compare learning-based hemodynamic maps with a conventional pushbroom-type hyperspectral imaging system

| | | Hyperspectral learning – Deep learning | | | Hyperspectral learning – Statistical learning | | |
|---|---|---|---|---|---|---|---|
| | | Oxygenated hemoglobin | Deoxygenated hemoglobin | Oxygen saturation | Oxygenated hemoglobin | Deoxygenated hemoglobin | Oxygen saturation |
| Conventional scanning system | Oxygenated hemoglobin | 0.936 | | | 0.905 | | |
| | Deoxygenated hemoglobin | | 0.985 | | | 0.978 | |
| | Oxygen saturation | | | 0.998 | | | 0.997 |

The maximum value of structural similarity index is 1.0 if two images are identical.

Figure 8A:
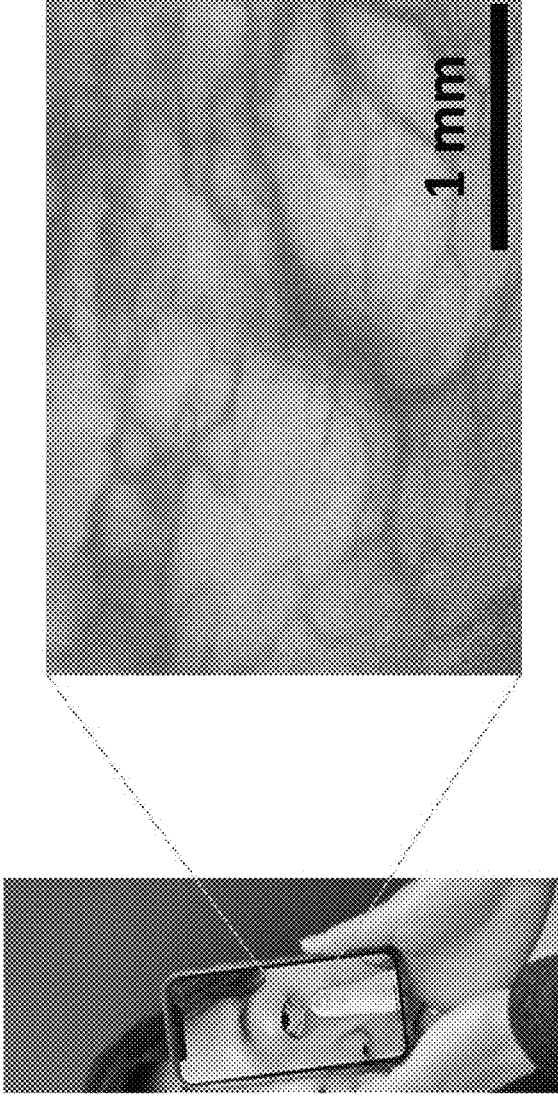
FIG. 8A is a photograph of a healthy adult volunteer taking a picture with a smartphone while the inner eyelid is pulled down including an RGB image of the inner eyelid with high spatial resolution showing the field-of-view.
Figure 8B:
FIG. 8B are the peripheral hemodynamic maps of Hb, $HbO_2$, and $sPO_2$ obtained during the resting state of a healthy adult volunteer.

As a model system for peripheral microcirculation in humans, we visualize spatiotemporal hemodynamic changes in the microvessels of the inner eyelid (i.e., the palpebral conjunctiva), shown in FIG. 8A, which is a photograph of a healthy adult volunteer taking a picture with a smartphone while the inner eyelid is pulled down including an RGB image of the inner eyelid with high spatial resolution showing the field-of-view. Microvessels in the inner eyelid are clearly visible without the effects of skin pigments, which are easily accessible for imaging. The inner eyelid is an easily accessible and highly vascularized peripheral tissue site that receives blood from the ophthalmic artery. Thus, the inner eyelid serves as a feasible sensing site for various diseases and disorders. FIG. 8B shows the peripheral hemodynamic maps of Hb, $HbO_2$, and $sPO_2$ obtained during the resting state of a healthy adult volunteer. In FIG. 8B, the $sPO_2$ maps reveal spatially complex patterns of perfusion in the inner eyelid, which are not evident in the photo (i.e., the RGB image).

It should be appreciated that the RGB camera and the spectrograph camera can be replaced with a microscope adapted, wherein the microscope includes a fiber optics spectrometer which receives light via a beam-splitter thereby obtaining hyperspectral and RGB data in the subarea and an RGB image of the field of interest. An example of such a microscope set up is MICROSPECTROSCOPY made by HORIBA SCIENTIFIC.

Incorporation of a spectroscopic analysis into a learning algorithm is also within the scope of the present disclosure. Tissue optics has been the cornerstone of biophotonics and biomedical optics to deepen our knowledge about light-tissue interactions and develop noninvasive optical diagnostic methods and devices. Light propagation in tissue can be explained by the theory of radiative transport and robust approximations (e.g. diffusion, Born, Monte Carlo simulation, and empirical modeling). An understanding of tissue optics allows us to ensure that the resulting outputs and learning algorithms are explainable and interpretable, overcoming the black box nature of deep learning.

Those having ordinary skill in the art will recognize that numerous modifications can be made to the specific implementations described above. The implementations should not be limited to the particular limitations described. Other implementations may be possible.

The invention claimed is:

1. A method of generating an image or video of a field of interest of a sample, comprising:

obtaining: i) a first Red-Green-Blue (RGB) image from about a field of interest of a sample, and ii) hyperspectral data from a subarea of the field of interest;

extracting an RGB image of the subarea from the first RGB image of the field of interest;

applying the hyperspectral data of the subarea to conduct a spectroscopic analysis of a sample, thereby generating spectral parameters for the subarea;

inputting i) the generated spectral parameters, and ii) the extracted RGB image of the subarea, collectively as training input data to a deep learning model;

training the deep learning model with the training input data thus generating a trained deep learning model;

obtaining a second RGB image about the field of interest including areas outside of the subarea;

inputting the second RGB image of the field of interest to the trained deep learning model;

outputting from the trained deep learning model a spectral map for the field of interest; and extracting hemodynamic parameters from the outputted spectral map of the field of interest; and determining oxygen saturation ($sPO_2$).

2. The method of claim 1, wherein the deep learning model is a neural network.

3. The method of claim 1, wherein the first and second RGB images of the field of interest are obtained as a photograph.

4. The method of claim 1, wherein the first and second RGB images of the field of interest are obtained from a video frame.

5. The method of claim 4, wherein the video has a frame rate of between about 960 frames per second and about 1920 frames per second.

6. The method of claim 1, wherein the first and second RGB images are obtained from a trichromatic camera.

7. The method of claim 1, wherein the hyperspectral data is obtained from an imaging spectrograph.

8. The method of claim 1, wherein the hyperspectral data is obtained from a spectrometer.

9. The method of claim 6, wherein the trichromatic camera is a smartphone camera.

10. The method of claim 6, wherein light from the sample is provided to the trichromatic camera via a mirror and a first plurality of lenses.

11. The method of claim 7, wherein the mirror includes a photometric slit adapted to provide light from the subarea.

12. The method of claim 7, wherein light exiting the photometric slit is diffracted by a diffraction grating and supplied to the imaging spectrograph via a second plurality of lenses.

13. The method of claim 7, position of the photometric slit on the mirror is selectable.

14. The method of claim 10, wherein the first and second RGB images from the field of interest are dividable into two or more subareas and for each said subarea, position of the photometric slit on the mirror is selectable.

15. The method of claim 1, wherein the first and second RGB images are obtained from a microscope combined with a fiber optics spectrometer via a beam-splitter thereby enabling obtaining hyperspectral and RGB data in the sub-area and an RGB image of the field of interest.

16. The method of claim 1, wherein the spectroscopic analysis of the sample is based on a sample optics domain knowledge model to generate the spectral parameters from the hyperspectral data.

17. The method of claim 14, wherein the sample optics domain knowledge model is based on one or more of theory of radiative transport, robust approximations, and Monte Carlo simulations.

18. The method of claim 15, wherein the robust approximations are based on one or more of diffusion, Born, and empirical modeling.

19. The method of claim 1, wherein the spectral parameters include hemodynamic parameters.

20. The method of claim 1, wherein the first RGB image is same as the second RGB image.

* * * * *